United States Patent [19]
Sogo et al.

[11] Patent Number: 6,159,708
[45] Date of Patent: *Dec. 12, 2000

[54] CHAPERONE EXPRESSION PLASMIDS

[75] Inventors: Kazuyo Sogo, Kyoto; Hideki Yanagi, Takarazuka; Takashi Yura, Kyoto, all of Japan

[73] Assignee: HSP Research Institute, Inc., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 09/100,110

[22] Filed: Jun. 19, 1998

[30] Foreign Application Priority Data

Jun. 20, 1997 [JP] Japan ................................ 9-180558

[51] Int. Cl.$^7$ .................................................. C12P 21/06
[52] U.S. Cl. .................................. 435/69.1; 435/252.33; 435/320.1; 435/488; 536/23.1; 536/23.2; 536/23.5; 536/23.51; 536/23.52; 536/23.53; 536/23.6; 536/23.7; 536/23.72; 536/24.1
[58] Field of Search ................................ 536/23.1, 23.2, 536/23.7, 23.5, 23.51, 23.52, 23.53, 23.6, 23.72, 24.1; 435/320.1, 252.33, 488, 69.1

[56] References Cited

FOREIGN PATENT DOCUMENTS

| | | |
|---|---|---|
| 8140671 | 6/1996 | Japan . |
| 8308564 | 11/1996 | Japan . |
| WO 85/03949 | 9/1985 | WIPO . |

OTHER PUBLICATIONS

Szabo, A. et al., *Proc. Natl. Science,* USA vol. 91, pp. 10345–10349 (Oct. 1994).
Blum, P. et al., *BioTechnol.* vol. 10, pp. 301–304 (Mar. 1992).
Perez–Perez, J. et al., *Biochem. Biophys. Res. Comm.* vol. 210, pp. 524–529 (May 1995).
Caspers, P. et al., *Cellular Molecular Biology,* vol. 40 pp. 635–644 (1994).
Stieger, M. and Caspers, P., *Immunology Methods Manual,* vol. 1, pp. 39–44 (1997) I. Lefkovitz, ed., Academic Press, San Diego.
Amrein, K.E. et al., *Proc. Natl. Acad. Sci. USA* vol. 92, pp. 1048–1052 (Feb. 1995).
Ashiuchi, M. et al., *J. Biochem,* vol. 117, pp. 495–498 (1995).
Dale, G.E. et al., *Protein Engineering* vol. 7, pp. 925–931 (1994).
Chang, A.C.Y. and Cohen, S.N., *Journal of Bacteriology* vol. 134, pp. 1141–1156 (Jun. 1978).
Zhou, Y.N. et al., *Journal of Bacteriology,* vol. 170, pp. 3640–3649 (Aug. 1988).
Kanemori, M. et al., *Journal of Bacteriology,* vol. 176, pp. 5648–5653 (Sep. 1994).
Kanemori, M. et al., *Journal of Bacteriology,* vol. 176, pp. 4235–4242 (Jul. 1994).
Namba, M. et al., *FEBS Letters,* vol. 353, pp. 124–128(1994).
Sawatani, M. et al., *Allergy,* vol. 43, pp. 467–473 (1994).
Nagai, H. et al., *Proc. Natl. Acad. Sci. USA* vol. 91, pp. 10280–10284 (Oct. 1994).
Ishiai, M. et al., *Journal of Bacteriology,* pp. 5597–5603 (Sep. 1992).
Tilly, K. and Georgopoulous, C., *Journal of Bacteriology,* vol. 149, pp. 1082–1088 (1982).
Ikeda, J. et al., *Biochemical Biophysical Research Communications,* vol. 230, pp. 94–99 (1997).
Wu, et al., "Enhanced Secretory Production...", Abstracts of the General Meeting of the American Society for Microbiology, vol. 15, No. 23, 1996, page 505.
Nishihara, et al., "Chaperone Coexpression Plasmids...", Applied and Environmental Microbiology, vol. 64, No. 5, May 1998, pp. 1694–1699.
Stieger, et al., "The Production of Soluble...", Academic Press LTD, Chap. 1.4, Oct. 1998, pp. 40–44.

*Primary Examiner*—Remy Yucel
*Attorney, Agent, or Firm*—Birch, Stewart, Kolasch & Birch, LLP

[57] ABSTRACT

An artificial operon comprising polynucleotides encoding each of chaperones DnaK, DnaJ and GrpE; an expression plasmid carrying the operon; a cotransformant prepared by introducing the expression plasmid into *E. coli* together with a foreign protein expression vector; and a method for producing a foreign protein comprising using the cotransformant.

23 Claims, 10 Drawing Sheets

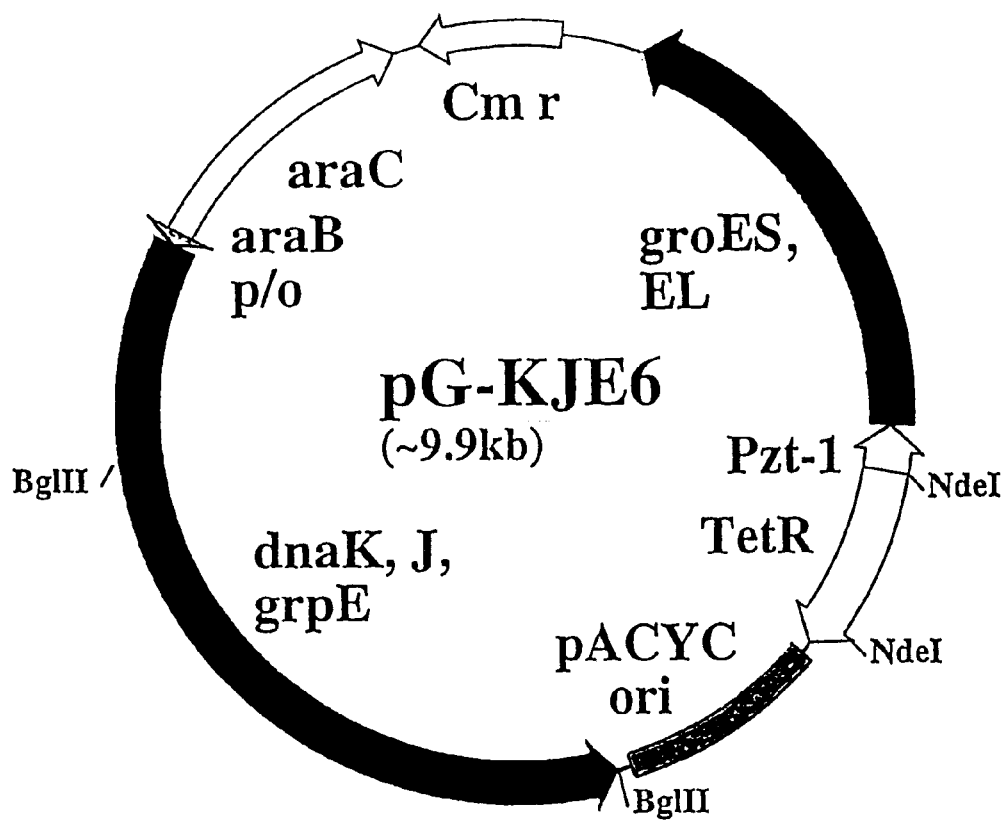
F I G. 1

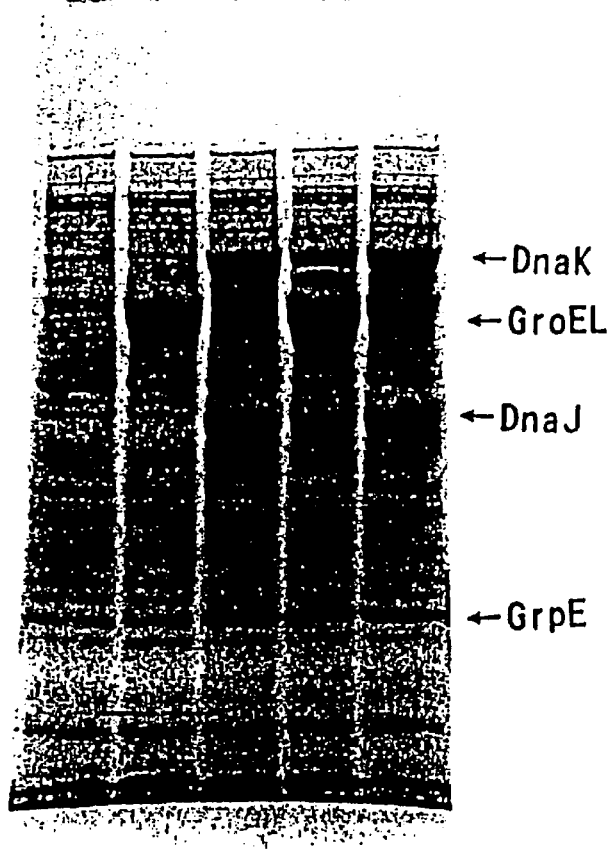
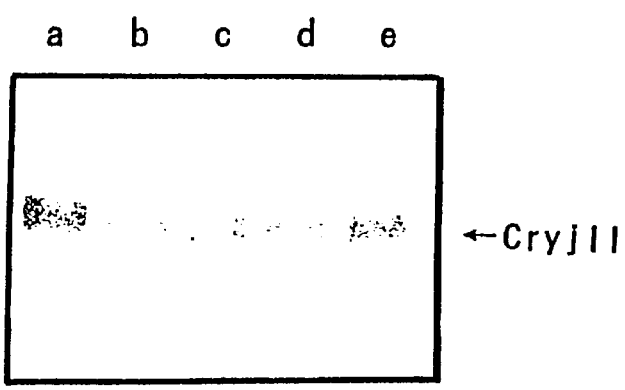
F I G. 8

CHAPERONE EXPRESSION PLASMIDS

BACKGROUND OF THE INVENTION

1. Field of the Invention

The present invention relates to a chaperone expression plasmid. More particularly, the present invention relates to an operon comprising polynucleotides encoding each of chaperones DnaK, DnaJ and GrpE; an expression plasmid carrying the operon; a cotransformant prepared by introducing the expression plasmid into *Escherichia coli* (hereinafter simply referred to as "*E. coli*") together with an expression vector for a foreign protein; and a method for producing a foreign protein using the cotransformant.

2. Discussion of the Related Art

*E. coli* serves ideally as a host for production of heterologous proteins at low costs and high yields, because it can easily be grown to high densities and the studies on the host-vector systems have been most advanced and many high-expression vectors have been developed. *E. coli* host-vector systems are, therefore, most widely utilized as expression systems for heterologous genes.

However, many heterologous proteins, especially eukaryotic proteins, associate with each other in cytoplasm and form biologically inactive insoluble aggregates known as "inclusion bodies" when expressed at high levels in *E. coli*. There is an advantage in formation of an inclusion body in that it is made possible to protect the expressed protein against degradation by proteases in host cells and to easily separate the inclusion body by centrifugation from the cells. In order to obtain the desired biologically active protein, however, it is necessary for the inclusion body to be denatured and solubilized, followed by renaturation (refolding). This solubilization-renaturation process is performed on the basis of repeated trial and error for individual proteins, but often fails to achieve satisfactory recovery rates. In some cases, renaturation is not always possible. Also, not a few heterologous proteins are degraded by proteases in *E. coli* and fail to achieve high expression levels. There have not yet been found a well-established means for solving such problems of insolubilization and degradation of expression products. Attempts to mass-produce biologically active proteins in *E. coli* have not always been altogether successful. In order to solve this problem, coexpression of chaperones and the like has been known, and a number of reports have been made.

DnaK, DnaJ and GrpE are chaperones that cooperatively act in protein folding. It has been considered that the ATP bound to DnaK is first hydrolyzed upon DnaJ binding to an unfolded protein substrate, resulting in the formation of an unfolded protein-DnaJ-DnaK (ADP binding type) complex, and thereafter ADP/ATP exchange takes place by GrpE, resulting in the release of the protein substrate from the complex [Szabo, A. et al., *Proc. Natl. Acad. Sci. USA* 91, 10345–10349 (1994)].

The dnaK and dnaJ genes are located at the same operon on the *E. coli* chromosome, while the grpE gene is located at a site apart from the above operon. To date, there have been reported a method of coexpression of a desired protein with DnaK alone or with both DnaK and DnaJ [Blum, P. et al., *BioTechnol.* 10, 301–304 (1992); Perez—Perez, J. et al., *Biochem. Biophys. Res. Comm.* 210, 524–529 (1995)]; a method of coexpression of a desired protein and DnaJ alone (Japanese Patent Laid-Open No. Hei 8-308564); a method of expression of DnaK and DnaJ, and of GrpE from respectively different plasmids [Caspers, P. et al., *Cell. Mol. Biol.* 40, 635–644 (1994)]; and a method of independent expression of DnaK and DnaJ and of GrpE from the same plasmid using the same promoter [Stieger, M. and Caspers, P., *Immunology Methods Manual*, 39–44 (1997)]. However, these methods have the drawbacks described below.

Specifically, DnaK, DnaJ and GrpE, which act in cooperation with each other, are expected to be more effective when coexpressed, and it is very likely that their inherent chaperone function is not fully exhibited simply when DnaK alone or only DnaK and DnaJ are expressed. Also, in the method in which DnaK and DnaJ, and GrpE, are expressed from the respectively different plasmids, since it is difficult for a total of three plasmids, including the expression plasmid for the desired protein, to coexist in *E. coli*, the gene for GrpE and the gene for the desired protein are placed on a single plasmid, which in turn necessitates that the expression plasmids need to be constructed to adapt to individual desired proteins. Moreover, since the same promoter is used for expression of GrpE and the desired protein, there arises a defect in that the expression of the desired proteins cannot be increased to sufficient levels. Further, in the method in which DnaK and DnaJ, and GrpE, are independently expressed from the same plasmid using the same promoter, another problem arises in the plasmid stability because of the presence of two units of the same promoter.

It has been well known to use protease mutants of *E. coli* as hosts to reduce the degradation of foreign proteins in *E. coli*. For example, deletion mutants for Lon proteases are preferably used. In addition, there has been known a method using rpoH mutants to suppress Lon and Clp proteases, since the induction of their expression is controlled by $\sigma^{32}$, encoded by the rpoH gene (Japanese Unexamined Patent Publication No. Sho 61-501307, WO 85/03949). Also, there has been known a method for stably expressing foreign proteins using double-mutants having mutations in the clpPX and lon genes (Japanese Patent Laid-Open No. Hei 8-140671).

It should be noted, however, that $\sigma^{32}$ also controls the induction of expression of chaperones, such as DnaK, DnaJ, GrpE, GroEL and GroES. GroEL and GroES are essential for the growth of *E. coli*, and rpoH deletion mutants cannot grow at temperatures exceeding 20° C. Therefore, missense mutations have conventionally been used for rpoH mutants (htpR mutants). It is desired, however, that the rpoH deletion mutants be used to more completely suppress the induction of expression of various proteases, such as Lon protease and Clp protease.

There have been reported a large number of successful cases of solubilization of foreign proteins that otherwise remain insolubilized in *E. coli* by coexpression of the foreign protein and GroEL and GroES. Examples thereof include, for instance, tyrosine kinase [Caspers, P. et al., *Cell Mol. Biol.* 40, 635–644 (1994); Amrein, K. E. et al., *Proc. Natl. Acad. Sci. USA* 92, 1048–1052 (1995)]; glutamate racemase [Ashiuchi, M. et al., *J. Blochem.* 117, 495–498 (1995)]; and dihydrofolate reductase [Dale, G. E. et al., *Protein Eng.* 7, 925–931 (1994)]. Other reported cases include improvement of solubility of human growth hormone by coexpression of DnaK [Blum, P. et al., *Biotechnol.* 10, 301–304 (1992)], transglutaminase solubilization by coexpression of DnaJ (Japanese Patent Laid-Open No. Hei 8-308564), and tyrosine kinase solubilization by coexpression of DnaK, DnaJ and GrpE [Caspers, P. et al., *Cell Mol. Biol.* 40, 635–644 (1994)]. It remains very difficult, however, to predict which foreign protein and which chaperone are to be coexpressed to what extent.

SUMMARY OF THE INVENTION

In view of the above problems in prior art, an object of the present invention is to provide an operon comprising polynucleotides encoding chaperones which can be used for expression of a foreign protein in the cells of *E. coli* in stabilized and solubilized form.

In one embodiment, the present invention provides an expression plasmid carrying the operon.

In another embodiment, the present invention provides a cotransformant prepared by introducing the expression plasmid into *Escherichia coli* together with a foreign protein expression vector.

In still another embodiment, the present invention provides a method for producing a foreign protein using the cotransformant.

These and other objects of the present invention will be apparent from the following description.

After extensive studies in consideration of the above-described problems, the present inventors have constructed a plasmid for expressing the dnaK, dnaJ and grpE genes joined together as a single operon under control of a single promoter. The present inventors have then succeeded in increasing the efficiency of protein folding in the DnaK/DnaJ/GrpE chaperone system by expressing DnaK, DnaJ and GrpE in *E. coli*. The present inventors also succeeded in enhancing the functions of both the DnaK/DnaJ/GrpE and GroEL/ES systems, the major chaperone systems in *E. coli*, and hence further increasing the efficiency of folding of the desired protein by inserting the groESgroEL gene onto the same plasmid as described above under control of another promoter, and expressing the gene product in *E. coli* mutants including protease mutants and rpoH mutants. In particular, the present inventors have made it possible to coexpress suitable amounts of DnaK, DnaJ and GrpE in the presence of supplemented GroEL and GroES, essential for the growth of rpoH mutants, and thereby they have succeeded in expressing the desired protein in stabilized and solubilized form.

In sum, the present invention pertains to the following:

(1) An artificial operon comprising polynucleotides encoding each of chaperones DnaK, DnaJ and GrpE;

(2) The artificial operon described in item (1) above, further comprising an inducible promoter;

(3) The artificial operon described in item (1) above, wherein the inducible promoter is selected from the group consisting of lac, trp, araB and Pzt-1;

(4) A plasmid carrying the artificial operon described in any one of items (1) to (3) above, usable for expression of DnaK, DnaJ and GrpE;

(5) The plasmid described in item (4) above, further comprising a groE operon ligated to an inducible promoter, the plasmid being capable for expression of DnaK, DnaJ, GrpE, GroEL and GroES;

(6) The plasmid described in item (5) above, wherein the inducible promoter ligated to a groE operon is selected from the group consisting of lac, trp, araB and Pzt-1;

(7) A cotransformant obtainable by introducing the plasmid described in any one of items (4) to (6) above into *E. coli* together with an expression vector for a foreign protein.

(8) The cotransformant described in item (7) above, wherein *E. coli* is a protease mutant;

(9) The cotransformant described in item (8) above, wherein the protease mutant is a lon-clpPX double mutant or a lon-clpPX-hslV/U triple mutant;

(10) The cotransformant described in item (7) above, wherein *E. coli* is a plsX mutant;

(11) The cotransformant described in item (7) above, wherein *E. coli* is an rpoH mutant;

(12) The cotransformant described in item (11) above, wherein the rpoH mutant is an rpoH deletion mutant;

(13) The cotransformant described in any one of items (7) to (12) above, wherein the foreign protein is selected from the group consisting of interferons, interleukins, interleukin receptors, interleukin receptor antagonists, granulocyte colony-stimulating factors, granulocyte macrophage colony-stimulating factors, macrophage colony-stimulating factors, erythropoietin, thrombopoietin, leukemia inhibitors, stem cell growth factors, tumor necrosis factors, growth hormones, proinsulin, insulin-like growth factors, fibroblast growth factors, platelet-derived growth factors, transforming growth factors, hepatocyte growth factors, bone morphogenetic factors, nerve growth factors, ciliary neurotrophic factors, brain-derived neurotrophic factors, glia cell line-derived neurotrophic factors, neurotrophine, prourokinase, tissue plasminogen activators, blood coagulation factors, protein C, glucocerebrosidase, superoxide dismutase, renin, lysozyme, P450, prochymosin, trypsin inhibitors, elastase inhibitors, lipocortin, reptin, immunoglobulins, single-chain antibodies, complement components, serum albumin, cedar pollen allergens, hypoxia-induced stress proteins, protein kinases, proto-oncogene products, transcription factors and virus-constituent proteins;

(14) A method for producing a foreign protein comprising using the cotransformant described in any one of items (7) to (13) above; and

(15) The method described in claim 14, wherein the cotransformant is cultured under the conditions for induction of chaperones that the expression levels of DnaK, DnaJ and GrpE, and the expression levels of GroEL and GroES are at levels suitable for stabilization and/or solubilization of the foreign protein.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein:

FIG. 1 is a schematic view showing a plasmid pG-KJE6;

FIG. 8 shows results of electrophoresis, wherein the upper panel shows an induction of expression of a chaperone, and the lower panel shows the expression of CryjII, each being evaluated by various concentrations of Ara and Tc in an rpoH deletion mutant;

DETAILED DESCRIPTION OF THE INVENTION

Figure 2:
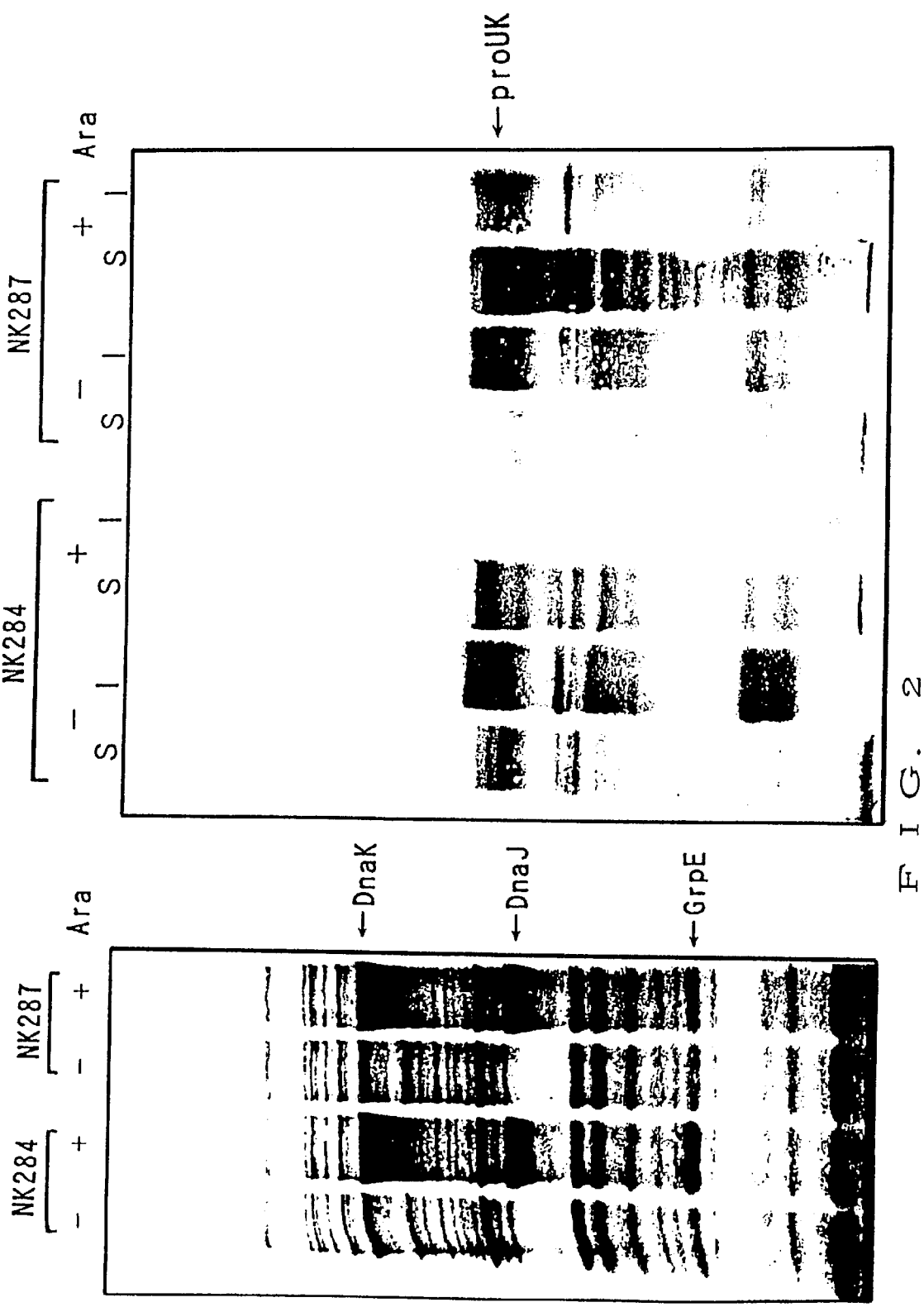
FIG. 2 shows results of electrophoresis of NK284 and NK287, wherein the left panel shows results of SDS-PAGE of an induction of expression of a chaperone by 1 mg/ml L-arabinose; and the right panel shows results of Western blotting showing a solubility of prourokinase (proUK), wherein S denotes a soluble fraction, and I denotes an insoluble fraction.

In the present invention, the chaperone may be any protein, as long as it is involved in protein folding. In the present invention, chaperones derived from *E. coli* are preferred. Examples of such chaperones include, for instance, DnaK, DnaJ, GrpE, GroEL, GroES, HscA/Hsc66, CbpA, HtpG, and the like. DnaK, DnaJ, GrpE, GroEL and GroES are more preferable from the viewpoint of expression of foreign proteins in a stabilized and solubilized form in *E. coli*. It is particularly preferable to use in combination with the DnaK/DnaJ/GrpE chaperone systems and the GroEL/GroES chaperone systems from the viewpoint of cooperative action of such chaperones.

The present invention provides an operon encoding the chaperone. The term "operon" used in the present invention is defined as a group of genes, each of which encodes the above-described chaperone, forming a transcription unit under the control of a single promoter, which includes a natural or artificial operon. In the present invention, it is preferable to use an artificial operon derived from *E. coli* comprising polynucleotides encoding DnaK, DnaJ and GrpE, which is referred to as dnaK/dnaJ/grpE operon. Also, it is more preferable to use the dnaK/dnaJ/grpE operon in combination with an operon comprising polynucleotides encoding GroEL and GroES, which is referred to as a groE operon, GroEL and GroES being required for the growth of *E. coli*.

The dnaK/dnaJ/grpE operon of the present invention is capable of more efficiently exhibiting the function of chaperones expressed than known dnaK/dnaJ operons. Concrete examples of using prourokinase as a foreign protein are given below.

From the viewpoint of regulation of the expression level of the chaperone of the present invention, it is preferable that the promoter controlling the transcription of the above-described operon be an inducible promoter. Examples of the inducible promoter include, for instance, lac, tac, trc, trp, araB, Pzt-1, λP$_L$, and the like. The lac, tac and trc promoters can be induced by using isopropyl-1-thio-β-D-galactopyranoside (IPTG); the trp, araB and Pzt-1 promoters can be induced by using 3-indoleacrylic acid (IAA), L-arabinose and tetracycline, respectively; and the ε P$_L$ promoter can be induced at a high temperature (42° C.). Also usable is a T7 promoter, which is specifically and strongly transcribed by a T7 RNA polymerase. In the transcription by T7 RNA polymerase, induction of the above T7 RNA polymerase by using IPTG is made possible using an *E. coli* strain harboring a lysogenized λ phage carrying the T7 RNA polymerase gene located downstream of the lac promoter.

The above-described promoters are contained in known vectors, and they can be used after being appropriately cut out from the respective vectors with restriction endonucleases, and the like.

The plasmid of the present invention has one of the above-described operons, and expresses one of the above-described chaperones after being introduced into *E. coli*. Accordingly, plasmids carrying a dnaK/dnaJ/grpE operon are preferred, with greater preference given to plasmids carrying both the dnaK/dnaJ/grpE operon and the groE operon.

As described above, these plasmids preferably express chaperones of the present invention, i.e., DnaK, DnaJ and GrpE, under the control of an inducible promoter, and they more preferably express DnaK, DnaJ, GrpE, GroEL and GroES under the control of an inducible promoter.

In order to optimize the level and timing of expression of the above-described chaperones without lowering the expression level of the desired protein, it is advantageous to independently control the expression of the chaperones and that of the desired protein. It is preferred that the inducible promoter used for chaperone expression differs from the promoter used to express the desired protein. Although the promoter used to express the dnaK/dnaJ/grpE operon and the promoter used to express the groE operon may be the same, the level and timing of expression of DnaK, DnaJ and GrpE and those of expression of GroEL and GroES can be separately regulated by using different promoters. For example, a plasmid pG-KJE6 (FIG. 1) is desirably used, wherein the plasmid comprises an araB promoter-dnaK/dnaJ/grpE operon and a Pzt-1 promoter-groE operon.

The pG-KJE6 is a plasmid constructed on the basis of a pACYC vector [Chang, A. C. Y. and Cohen, S. N., *J. Bacteriol.* 134, 1141–1156 (1978)]. As shown in FIG. 1, the pG-KJE6 has a structure comprising a pACYC vector-derived ori, a Cm resistance gene, the araB promoter-dnaK/dnaJ/grpE operon, and the Pzt-1 promoter-groE operon. Expression of DnaK, DnaJ and GrpE is induced by using L-arabinose, and that of GroEL and GroES is induced by using tetracycline. By adding L-arabinose and tetracycline at the same time, separately with time intervals, or at different concentrations, these two groups of chaperones can be expressed at the same time, or separately with time intervals, or at different levels as occasion demands.

Two mutually closely related plasmids cannot usually stably co-exist in the same host. This phenomenon is known as incompatibility. Any plasmid can serve as the plasmid of the present invention, as long as it has a replicon showing no incompatibility in *E. coli* with the expression vector for the desired protein. When pBR322 or another expression vector having the Col E1 replicon, for example, is used as an expression vector for the desired protein, the p15A replicon, existing in a pACYC vector, can be used for the plasmid of the present invention.

The plasmid of the present invention may further contain a selection marker gene as occasion demands in order to facilitate selection upon transformation. Examples of such selection marker genes include ampicillin resistance (Amp$^r$) genes, kanamycin resistance (Km$^r$) genes, and chloramphenicol resistance (Cm$^r$) genes. It is desired that the selection marker gene used be different from the selection marker gene contained in the foreign protein expression vector.

The above-described plasmids can be constructed by a method, for example, described in *Molecular Cloning: A Laboratory Manual*, 2nd ed., Sambrook, J. et al., Cold Spring Harbor Laboratory Press, New York, 1989. The construction of the above-described plasmid pG-KJE6 is concretely described in Examples set forth below.

Methods for expression of the chaperone of the present invention using an inducible promoter, and methods for regulation of the expression levels of the chaperone of the present invention, using the above-described plasmids, are described below.

In the present invention, the term "a cotransformant" refers to that obtainable by introducing one of the above-described plasmids together with a foreign protein expression vector into *E. coli*.

Any expression vector for expression of a foreign protein can serve for the present invention, as long as it causes the desired foreign protein to be expressed in *E. coli*, and as long as it does not exhibit incompatibility with the above-described plasmids. A preference is given to a vector wherein the expression of the desired foreign protein is induced by an inducible promoter.

The inducible promoters for expression of a foreign protein include the same promoters as those for expression of the chaperone described above. The expression of a chaperone of the present invention and that of the desired foreign protein can be separately induced by using an appropriate promoter different from that used to induce the expression of the chaperone of the present invention.

Also, the expression vector for expression of a foreign protein may contain a selection marker gene as occasion demands. Such selection marker genes include the same as those for expression of the chaperone described above. A double selection of cotransformants is made possible by using a selection marker gene other than that contained in the plasmid of the present invention.

*E. coli* strains usable in the present invention include wild strains, such as HB101, JM109, MC4100, MG1655 and W3110; and various mutants, including protease mutants, such as lon mutants, clpPX mutants, hslV/U mutants, lon-clpPX double mutants and lon-clpPX-hslV/U triple mutants; plsX mutants; rpoH deletion mutants; and rpoH missense mutants.

In the present invention, protease mutants, such as lon mutants, clpPX mutants, hslV/U mutants, lon-clpPX double mutants and lon-clpPX-hslV/U triple mutants; plsX mutants; and rpoH mutants, such as rpoH deletion mutants, can be favorably used to more stably express foreign proteins.

A preferable lon-clpPX double mutant is *E. coli* strain KY2263 (FERM BP-6238) derived from *E. coli* strain MC4100, prepared by introducing double deletion mutations in the lon and clpPX genes. The *E. coli* KY2263 has been deposited under accession number FERM BP-6238 with the National Institute of Bioscience and Human-Technology, Agency of Industrial Science and Technology, Ministry of International Trade and Industry, of which the address is 1-3, Higashi 1-chome, Tsukuba-shi, Ibaraki-ken, 305-0046, Japan; date of original deposit: Feb. 18, 1997; and date of transfer request from the original deposit to the International Deposit under the Budapest Treaty: Jan. 26, 1998.

Also, the term "lon-clpPX-hslV/U triple mutant" refers to a mutant prepared by introducing mutation in the above-described lon-clpPX double mutant and further in the hslV/U gene, which encodes HslV/U protease. A preference is given to *E. coli* strain KY2266 (FERM BP-6239) derived from *E. coli* strain MC4100, prepared by incorporating triple deletion mutations in the lon, clpPX and hslV/U genes. The *E. coli* KY2266 has been deposited under accession number FERM BP-6239 with the National Institute of Bioscience and Human-Technology, Agency of Industrial Science and Technology, Ministry of International Trade and Industry, of which the address is 1-3, Higashi 1-chome, Tsukuba-shi, Ibaraki-ken, 305-0046, Japan; date of original deposit: Feb. 18, 1997; and date of transfer request from the original deposit to the International Deposit under the Budapest Treaty: Jan. 26, 1998.

Also, examples of the plsX mutants include, for instance, a plsX mutant having a mutation of insertion of the tetracycline resistance gene into a position corresponding to the N-terminal region of a polypeptide encoded by plsX (Japanese Patent Laid-Open No. Hei 8-140671).

Examples of the rpoH deletion mutants include, for instance, *E. coli* MC4100 ΔrpoH [Zhou, Y. N. et al., *J. Bacteriol.* 170, 3640–3649 (1988)], *E. coli* MG1655 ΔrpoH, and the like. In the rpoH deletion mutants, the expression levels of all heat shock proteins controlled by $\sigma^{32}$, including chaperones and proteases, are lowered. By sufficiently supplementing such chaperones having their expression suppressed by transformation of the rpoH deletion mutants with, for example, pG-KJE6, it is expected that a system of low protease contents and high chaperone contents can be provided with favorable effects for stable expression of unstable foreign proteins. Also, the rpoH deletion mutants are sensitive to temperature, and they usually cannot grow at temperatures exceeding 20° C. By supplementing GroEL and GroES as described above, the rpoH deletion mutants can grow at temperatures exceeding 20° C., and hence facilitating their handling. It is, therefore, particularly preferable to use the rpoH deletion mutant.

In the present invention, the foreign protein to be expressed may be any protein, as long as it is a foreign protein that is expressed in unstabilized form and/or insolubilized form in *E. coli*. Such foreign proteins include interferons, interleukins, interleukin receptors, interleukin receptor antagonists, granulocyte colony-stimulating factors, granulocyte macrophage colony-stimulating factors, macrophage colony-stimulating factors, erythropoietin, thrombopoietin, leukemia inhibitors, stem cell growth factors, tumor necrosis factors, growth hormones, proinsulin, insulin-like growth factors, fibroblast growth factors, platelet-derived growth factors, transforming growth factors, hepatocyte growth factors, bone morphogenetic factors, nerve growth factors, ciliary neurotrophic factors, brain-derived neurotrophic factors, glia cell line-derived neurotrophic factors, neurotrophine, prourokinase, tissue plasminogen activators, blood coagulation factors, protein C, glucocerebrosidase, superoxide dismutase, renin, lysozyme, P450, prochymosin, trypsin inhibitors, elastase inhibitors, lipocortin, reptin, immunoglobulins, single-chain antibodies, complement components, serum albumin, cedar pollen allergens, hypoxia-induced stress proteins, protein kinases, proto-oncogene products, transcription factors and virus-constituent proteins.

A calcium chloride method, a rubidium chloride method, an electoporation method and other conventional methods can be employed to introduce the plasmid of the present invention together with an expression vector for a foreign protein into E. coli. Screening for cotransformants can be carried out using chemicals appropriate for selection marker genes. Expression of the foreign protein can, for example, be confirmed by such means as Western blotting.

The present invention further provides a method for producing a foreign protein using the above-described cotransformant. The method comprises three steps:

(1) checking chaperone induction conditions for stabilization and/or solubilization of a foreign protein subject to expression;

(2) culturing a cotransformant to induce expression of chaperones and the foreign protein under the induction conditions checked in (1) above, and harvesting the cells; and (3) disrupting of the harvested cells, and isolating and purifying the foreign protein using a purification method depending upon the foreign protein.

First, by taking an example of expression of prourokinase as a foreign protein, it is possible to specifically check that the chaperone function can be more effectively exhibited by coexpression of mutually cooperating DnaK, DnaJ and GrpE using the dnaK/dnaJ/grpE operon of the present invention, as compared to a case where only DnaK and DnaJ are expressed using a known dnaK/dnaJ operon.

A plasmid pAR3 (ATCC87026), the plasmid derived from the pACYC vector, and carrying a Cm resistance gene and araC and araB promoter/operator genes, is cleaved with a restriction endonuclease PstI at a position downstream of the araB promoter, and the resulting cleaved plasmid is blunt-ended. Thereafter, an about 3 kb coding region of the E. coli dnaK/dnaJ operon prepared by PCR and an about 0.6 kb coding region of the grpE gene are inserted into appropriate sites to prepare a plasmid pKJE7 for expression of DnaK, DnaJ and GrpE from a single operon under the control of the araB promoter.

Next, the plasmid pKJE7 is cleaved with restriction endonucleases BspHI and KpnI to remove almost the entire coding region of the grpE gene, and the resulting cleaved plasmid is blunt-ended. Thereafter, the resulting plasmid is self-ligated. A plasmid for expression of only DnaK and DnaJ under the control of the araB promoter is isolated and named as pKJ1.

Next, E. coli MG1655 (CGSC6300; made available by E. coli Genetic Stock Center, Yale University) is transformed by the rubidium chloride method with an IPTG-inducible plasmid pUK-02pm0 [Kanemori, M. et al., J. Bacteriol. 176, 5648–5653 (1994)], and one of the plasmid pKJE7 and the plasmid pKJ1 prepared above. The resulting cotransformant with pUK-02pm0 and pKJE7 and the resulting cotransformant with pUK-02pm0 and pKJ1 are isolated, and named as cotransformants NK284 and NK287, respectively.

Each of the cotransformants NK284 and NK287 prepared above are respectively cultured at 37° C. in L broth supplemented with 1 mg/ml L-arabinose. When Klett Unit reaches about 40, 1 mM IPTG is added to the culture. After culturing for one hour, a portion of the culture is taken, and trichloroacetic acid is added so as to give a final concentration of 5% to precipitate the cells. Each of the precipitates is collected by centrifugation and washed with acetone. Thereafter, the washed cells are dissolved in a sample buffer for SDS-PAGE, and proteins are separated by SDS-PAGE, followed by detection of induced chaperones by CBB staining (FIG. 2, left panel).

The cells of each of NK284 and NK287 recovered by centrifugation of the remaining portion of the culture mentioned above are disrupted by sonication. Thereafter, the disrupted cells are fractionated by centrifugation into a soluble fraction and an insoluble fraction to detect prourokinase in each fraction by Western blotting using an antibody against urokinase (FIG. 2, right panel).

It is clear from FIG. 2 that when DnaK, DnaJ and GrpE are coexpressed, almost entire prourokinase are expressed in a soluble form, whereas when only DnaK and DnaJ are coexpressed, the prourokinase expressed is only partially solubilized, the remaining being expressed in an insoluble form.

The method for producing a foreign protein using a cotransformant NK241 by using the plasmid pG-KJE6 and an expression vector for a cedar pollen allergen, such as a *Cryptomeria japonica* pollen allergen CryjII will be explained concretely hereinbelow. When expressed in E. coli, the CryjII is an unstable protein, its half-life is about ten minutes as determined by Western blotting of the amount of CryjII remaining in cells in which protein synthesis is blocked by addition of spectinomycin.

Figure 3:
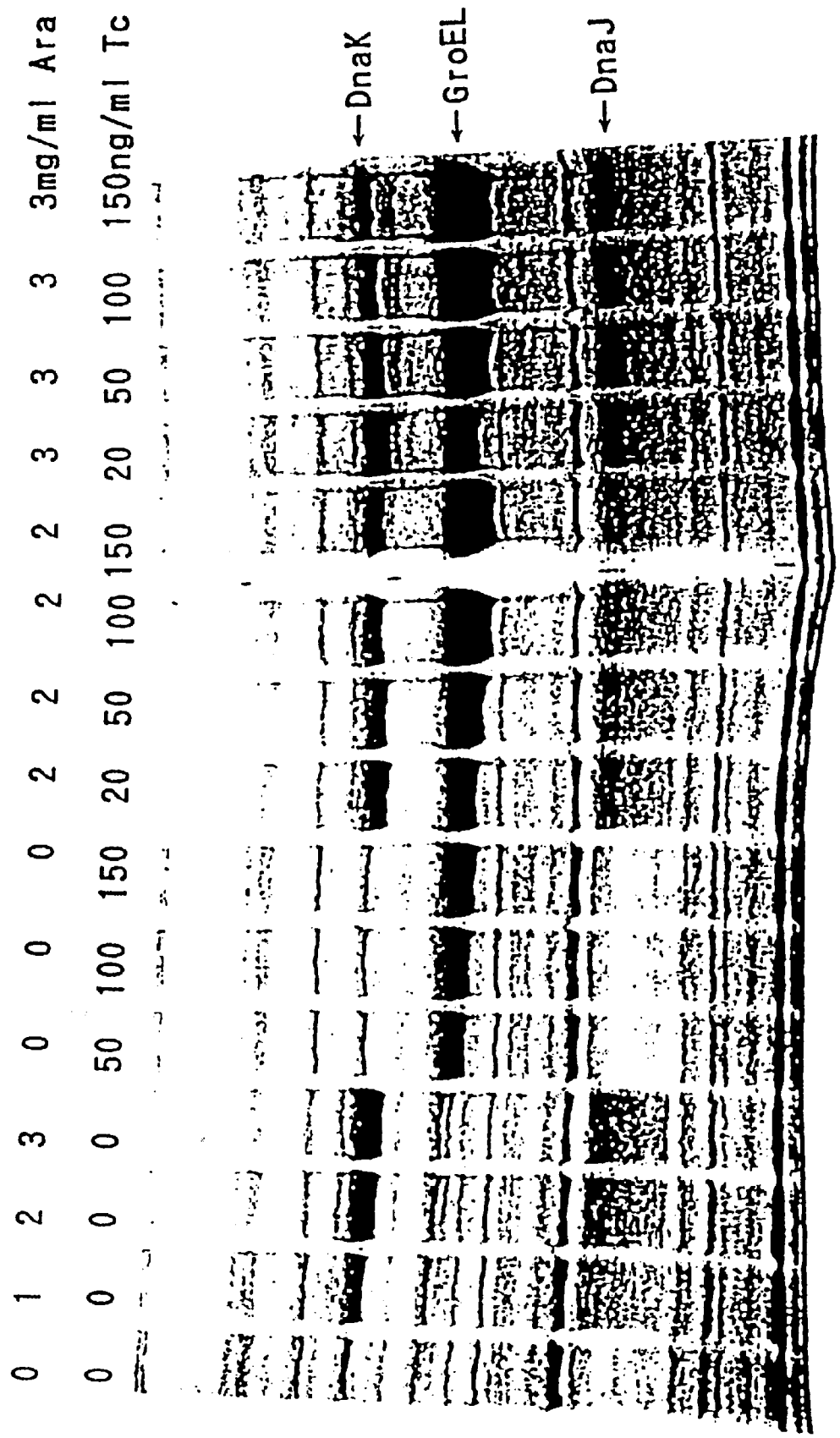
FIG. 3 shows results of SDS-PAGE showing an induction of expression of a chaperone from pG-KJE6 in JM109, wherein the numerical figures on each lane indicate concentrations of L-arabinose (Ara) and tetracycline (Tc)

(1) Studies on Conditions for Chaperone Induction Suitable for Stabilization and/or Solubilization of CryjII First, E. coli JM109 is transformed with pG-KJE6 alone, and a transformant is obtained by selection with chloramphenicol. The resulting transformant is cultured at 30° C. in an L broth supplemented with 0 to 3 mg/ml L-arabinose and 0 to 150 ng/ml tetracycline. When Klett Unit reaches about 40, trichloroacetic acid is added to the culture so as to give a final concentration of 5% to precipitate the cells. Thereafter, the proteins are separated by SDS-PAGE, followed by detection of induced chaperones by Coomassie brilliant blue (CBB) staining (FIG. 3). As shown in FIG. 3, each of chaperones is induced which is concentration-dependent on the chemicals used.

Figure 4:
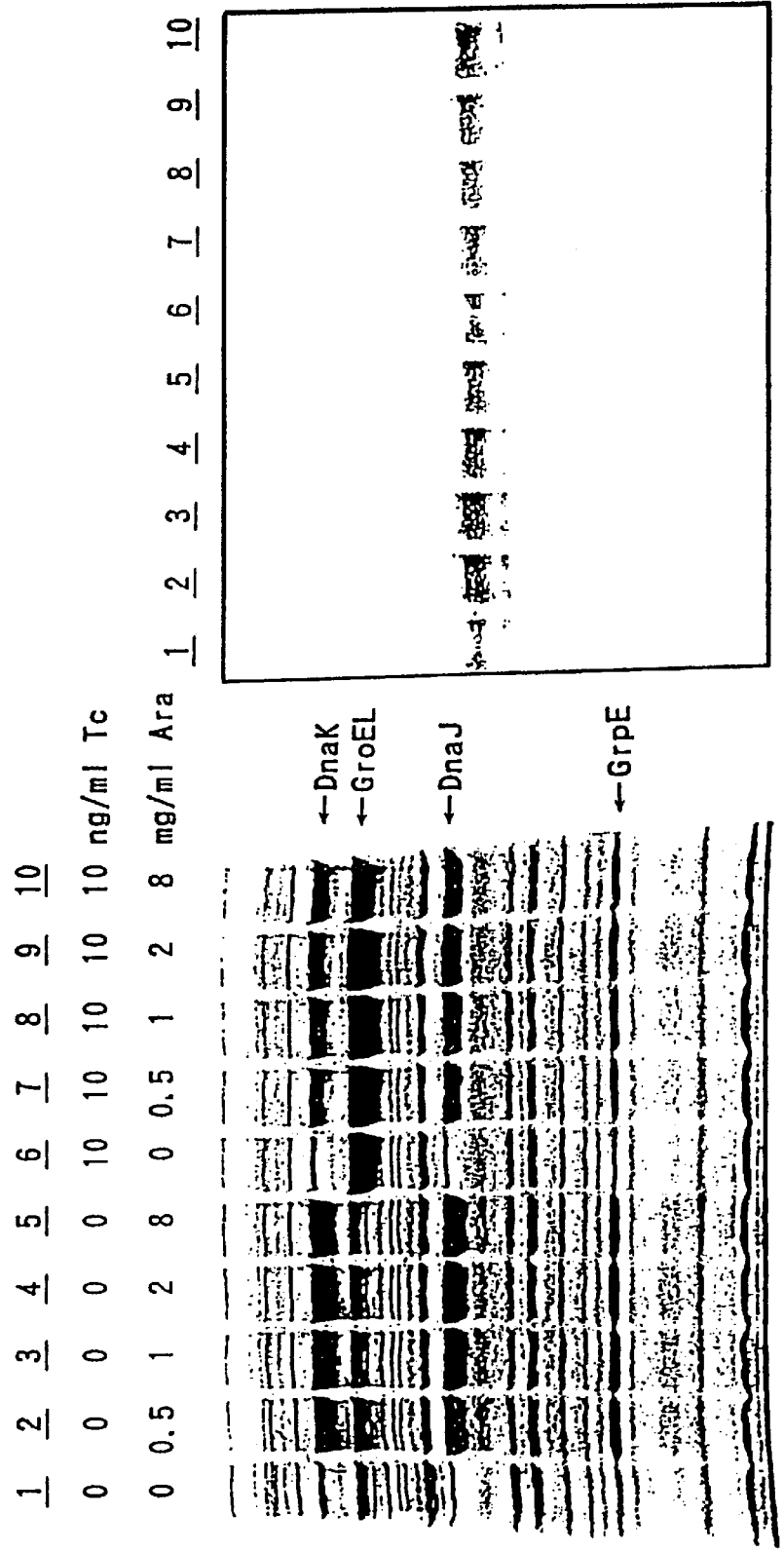
FIG. 4 shows results of electrophoresis of NK241, wherein the left panel shows an induction of expression of a chaperone by various concentrations of Ara and Tc; and the right panel shows an expression of CryjII.

Next, NK241, which is an MG1655 cotransformant with pG-KJE6 and an IPTG-inducible expression vector for CryjII is cultured in the same manner as described above, except that 0 to 8 mg/ml L-arabinose and 0 to 10 ng/ml tetracycline are added. When Klett Unit reaches about 40, 1 mM IPTG is added to the culture. After culturing for two hours, a portion of the culture is taken, and trichloroacetic acid is added so as to give a final concentration of 5% to precipitate the cells. Thereafter, the proteins are separated by SDS-PAGE, followed by detection of induced chaperones by CBB staining or detection of CryjII by Western blotting (FIG. 4). As shown in FIG. 4, when DnaK, DnaJ and GrpE are coexpressed, or GroEL and GroES are coexpressed, or all five proteins are coexpressed, the CryjII is expressed in a high level.

Figure 5:
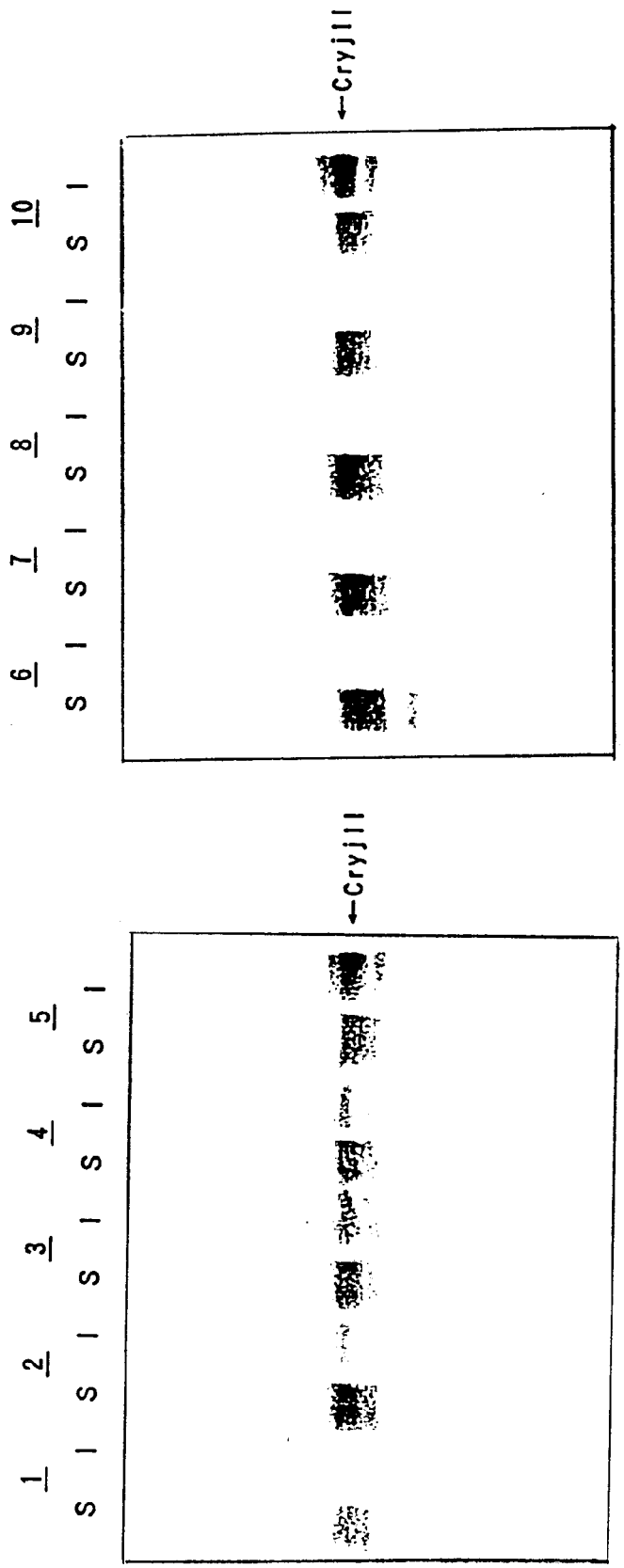
FIG. 5 shows results of electrophoresis showing a property (solubility) of CryjII in a fraction prepared by fractionating the same samples in each lane of FIG. 4 to a soluble fraction and an insoluble fraction, wherein S denotes a soluble fraction, and I denotes an insoluble fraction.

Also, the cotransformant recovered by centrifugation of the remaining portion of the culture is disrupted by sonication. Thereafter, the disrupted cells are fractionated by centrifugation into a soluble fraction and an insoluble fraction to detect solubility of CryjII in each fraction by Western blotting (FIG. 5). As shown in FIG. 5, CryjII is expressed in an insoluble form when only DnaK, DnaJ and GrpE are coexpressed (lanes 2 to 5), while it is stabilized in a soluble form when expression of GroEL and GroES is induced at the same time in the presence of relatively low amounts of DnaK, DnaJ and GrpE expressed (lanes 6 to 9). When DnaK, DnaJ and GrpE are expressed in great excess, however, CryjII is expressed in an insoluble form even when expression of GroEL and GroES is induced at the same time (lane 10). It is, therefore, seen that when expression of GroEL and GroES is induced at the same time, CryjII insolubilization owing to overexpression of DnaK, DnaJ and GrpE is suppressed to a certain extent.

CryjII stabilization can be shown as a half-life by quantitating by Western blotting the amount of CryjII remaining in the cells in which protein synthesis is blocked by addition of spectinomycin. Under the conditions shown above, the half-life is 40 minutes or more (FIG. 6).

Figure 7:
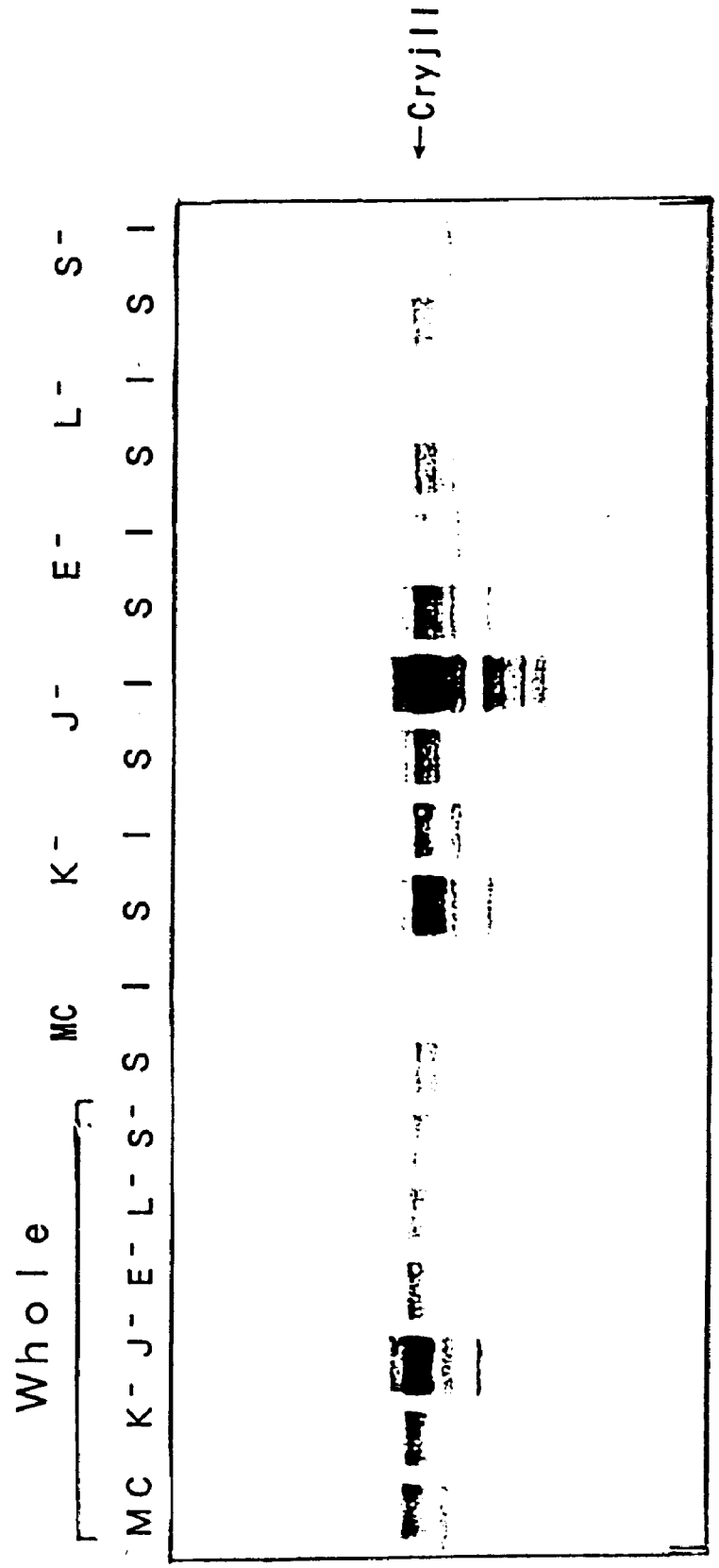
FIG. 7 shows results of electrophoresis showing expression of CryjII in various chaperone mutants, wherein MC denotes a parent strain MC4100, K⁻ denotes C4100 ΔdnaK52, J⁻ denotes MC4100 ΔdnaJ259, E⁻ denotes MC4100 grpE280, L⁻ denotes MC4100 groEL44, and S⁻ denotes MC4100 groES72, and wherein S denotes a soluble fraction, and I denotes an insoluble fraction.

In order to further clarify the effects of the chaperones on expression of CryjII, the above-described CryjII expression vector is introduced into each of DnaK, DnaJ, GrpE, GroEL and GroES mutants derived from MC4100 strain, and the expression and solubility of CryjII are examined in the same manner as described above (FIG. 7). As shown in FIG. 7, CryjII is expressed in an insoluble form in the DnaK mutant and the DnaJ mutant, while it is hardly affected in the GrpE mutant. It can be deduced that CryjII is soluble but more unstable with reduced expression levels in the GroEL mutant and the GroES mutant.

In consideration of these results, it is suggested that DnaK, DnaJ and GrpE have important effects on the CryjII folding, because the CryjII is expressed in an insoluble form when DnaK, DnaJ and GrpE are expressed in excess or in shortage.

Figure 9:
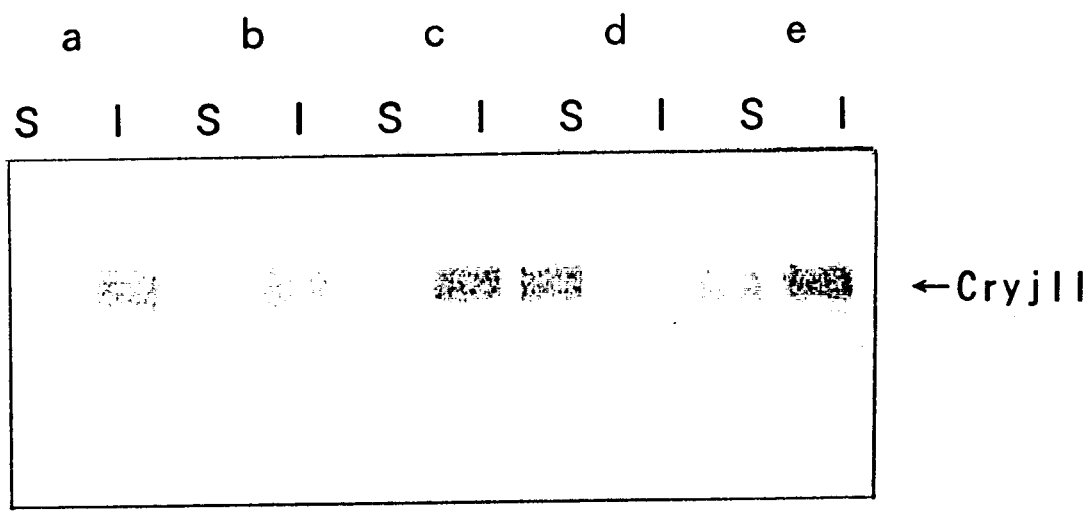
FIG. 9 shows results of electrophoresis showing solubility of CryjII by fractionating the same samples of each lane of FIG. 8 into a soluble fraction and an insoluble fraction, wherein S denotes a soluble fraction, and I denotes an insoluble fraction.

Next, the chaperones involved in the CryjII folding are studied in further detail in the same manner as described above, using an rpoH deletion mutant cotransformant, NK196 (FIGS. 8 and 9). As shown in FIGS. 8 and 9, in the rpoH deletion mutant, the CryjII expressed is very stable but is expressed in a considerably insoluble form because of the reduced amounts of a set of chaperones and proteases (FIGS. 8 and 9, lane "a"). Also, regarding the CryjII solubilization, when only three of DnaK, DnaJ and GrpE, or only two of GroEL and GroES, are coexpressed, CryjII is not solubilized (FIG. 9, lanes "b" and "c"). CryjII is solubilized for the first time when all five of DnaK, DnaJ, GrpE, GroEL and GroES are coexpressed (FIG. 9, lane "d"). Furthermore, when the expression levels of DnaK, DnaJ and GrpE are further increased under the conditions for coexpression of the above-mentioned five proteins, re-insolubilization of CryjII takes place (FIG. 9, lane "e"), yielding the experimental results which are consistent with those obtained with NK241.

When combined together, the above-described results lead to the following hypothesis: GroEL and GroES bind to CryjII to inhibit the above CryjII degradation by proteases without being much involved in CryjII folding. On the other hand, DnaK, DnaJ and GrpE are closely associated with CryjII folding, with an important role probably played by DnaJ, in particular. However, expression of DnaK, DnaJ and GrpE in excess would make CryjII in an insoluble form. Thus, in order to carry out CryjII folding efficiently, it is desired that two chaperone groups, i.e., the group of DnaK, DnaJ and GrpE, and the group of GroEL and GroES, are present in appropriate amounts. This hypothesis agrees well with the existing hypotheses of mutual cooperation of the chaperones.

It is novel to study the effects of the five chaperones of DnaK, DnaJ, GrpE, GroEL and GroES on expression of a foreign protein by coexpressing them at the same time or in groups, and their effective expression. Studying proteins, such as CryjII, of which behaviors change depending on the kinds and amounts of the chaperones coexpressed is highly interesting from the viewpoint of the understanding of chaperone action. Also, the systems in which only chaperones are overexpressed in the rpoH deletion mutants seem to be applicable to more efficient expression of other foreign proteins as well.

(2) Cultivation of NK241, Inductive Expression of Chaperones and Foreign Proteins, and Recovery of Cells The NK241 is cultured in the same manner as in (1) above, under suitable chaperone induction conditions thus obtained for expression of CryjII in a stable and soluble form (10 ng/ml tetracycline and 1 mg/ml L-arabinose). When Klett Unit reaches about 40, 1 mM IPTG is added to the culture, and the cells are harvested after culturing for two hours.

(3) Isolation and Purification of CryjII

After the harvested cells are disrupted, the supernatant is recovered by such as centrifugation. The resulting supernatant is subjected to conventional purification methods for proteins, such as gel filtration and various column chromatographies, to purify CryjII.

Figure 10:
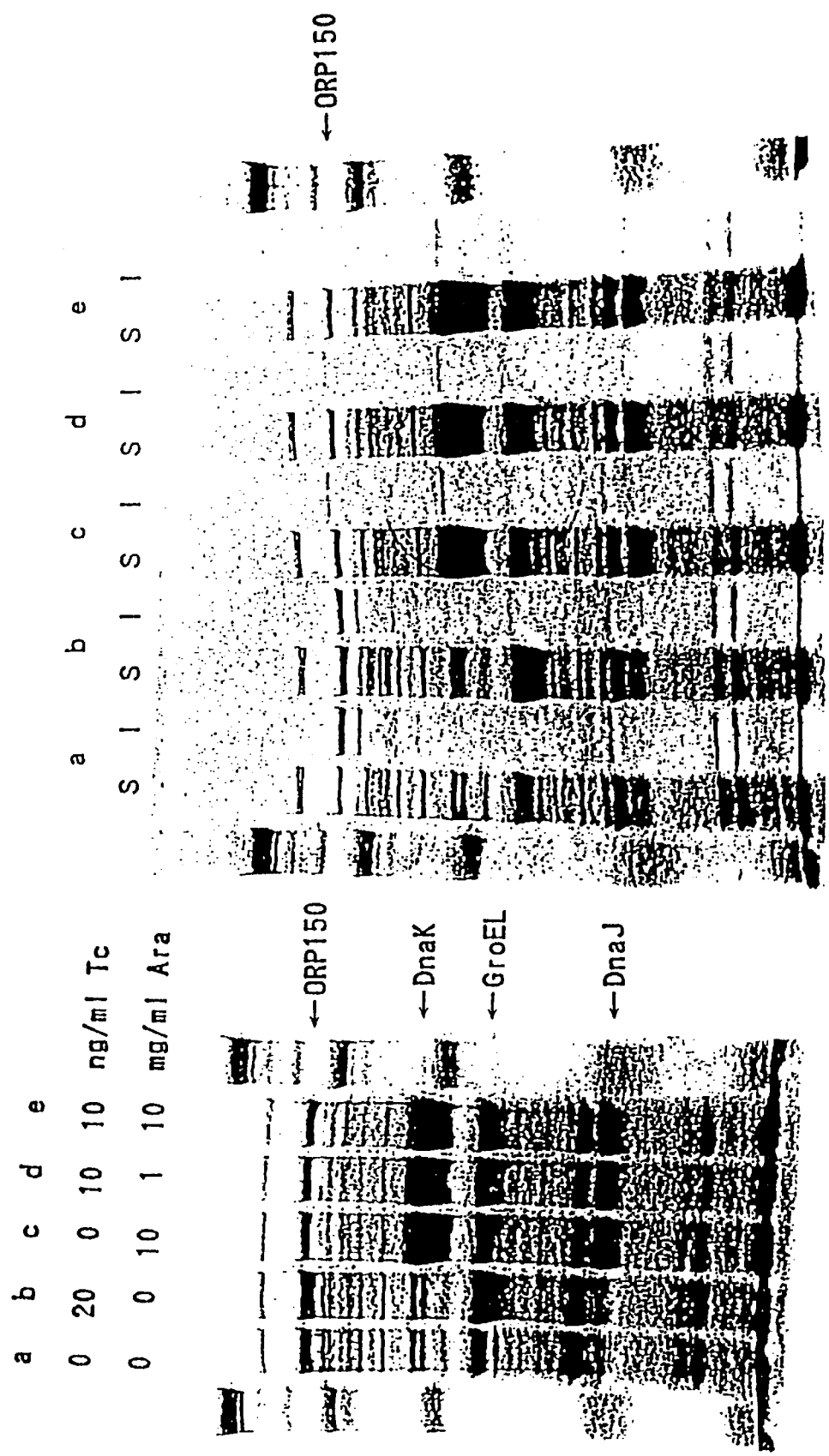
FIG. 10 shows results of electrophoresis, wherein the upper panel shows an induction of expression of a chaperone, and the lower panel shows the expression of ORP150, each being evaluated by various concentrations of Ara and Tc in an rpoH deletion mutant, wherein both ends of the lane in each panel indicate molecular weight markers, and where in the right panel S denotes a soluble fraction, and I denotes an insoluble fraction.

In another embodiment of the present invention, human ORP150 is produced using a cotransformant NK269 prepared by introducing into *E. coli* JM109 an expression vector pORP4 (induced with IPTG) for a human hypoxia-induced stress protein ORP150, and pG-KJE6. When human ORP150 is expressed in *E. coli* using pORP4 alone, the expressed ORP150 is mostly insoluble. Since NK269 cannot grow for unknown reasons, when L-arabinose is added to the culture at the initiation time of cultivation, NK269 is cultured to induce expression of human ORP150 in the same manner as above, except that L-arabinose and tetracycline are added when Klett Unit reaches about 40 (FIG. 10). As shown in FIG. 10, not less than half the human ORP150 produced appears in the soluble fraction when only GroEL and GroES are coexpressed (right panel, lane "b"), and it is mostly soluble when only three of DnaK, DnaJ and GrpE or all the above-described five are expressed at the same time (right panel, lanes "c", "d" and "e").

Human ORP150 is, therefore, produced, for example, as follows: NK269 is cultured in L broth. When Klett Unit reaches about 40, 10 ng/ml tetracycline, 10 mg/ml L-arabinose and 1 mM IPTG are added to the culture to induce expression. After 2 hours of cultivation, the cells are harvested in the same manner as above, followed by isolation and purification of ORP150.

EXAMPLES

The present invention will be hereinafter described in more detail by means of the following examples, without intending to restrict the scope or spirit of the present invention thereto. Unless otherwise specified, the following examples were carried out by the methods described in Sambrook, J. et al., *Molecular Cloning: A Laboratory Manual*, 2nd ed., Cold Spring Harbor Laboratory Press, New York, published in 1989, *Current Protocols in Protein Science* (ed. coligan, J. E. et al.), John Wiley and Sons, Inc., etc.

Example 1

Preparation of pKJE7

A plasmid pAR3 (ATCC87026), derived from a pACYC vector, and carrying a Cm resistance gene and araC and araB promoter/operator genes, was cleaved with a restriction endonuclease PstI at a position downstream of the araB promoter, and the resulting cleaved plasmid was blunt-ended. Thereafter, an about 3 kb coding region of the *E. coli* dnaK/dnaJ operon prepared by PCR and an about 0.6 kb coding region of the grpE gene were inserted into appropriate sites to prepare a plasmid pKJE7 for expression of DnaK, DnaJ and GrpE from a single operon under the control of the araB promoter.

Comparative Example 1

Preparation of pKJ1

The plasmid pKJE7 prepared in Example 1 was cleaved with restriction endonucleases BspHI and KpnI to remove almost the entire coding region of the grpE gene, and the resulting cleaved plasmid was blunt-ended. Thereafter, the resulting plasmid was self-ligated. A plasmid for expression of only DnaK and DnaJ under the control of the araB promoter was isolated and named as pKJ1.

Example 2

Preparation of NK284 Cotransformant

*E. coli* MG1655 (CGSC6300; made available by *E. coli* Genetic Stock Center, Yale University) was transformed by the rubidium chloride method with 10 ng of a plasmid pUK-02pm0 [Kanemori, M. et al., *J. Bacteriol.* 176, 5648–5653 (1994)], and 10 ng of the plasmid pKJE7 prepared in Example 1, the plasmid pUK-02pm0 being capable of inducing expression of human prourokinase with IPTG. The resulting cotransformant with pUK-02pm0 and pKJE7 was isolated by selection with chloramphenicol and ampicillin, and named as a cotransformant NK284.

Comparative Example 2

Preparation of NK287 Cotransformant

Same procedures as in Example 2 were carried out except that the plasmid pKJ1 prepared in Comparative Example 1 was used in place of the plasmid pKJE7 in Example 2. A cotransformant with pUK-02pm0 and pKJ1 was isolated and named as a cotransformant NK287.

Test Example 1

Expression of Prourokinase Using NK284 and NK287

The cotransformant NK284 prepared in Example 2 and the cotransformant NK287 prepared in Comparative Example 2 were respectively cultured at 37° C. in L broth supplemented with 1 mg/ml L-arabinose (manufactured by Wako Pure Chemical Industries). When Klett Unit reached about 40, 1 mM IPTG (manufactured by Wako Pure Chemical Industries) was added to the culture. After culturing for one hour, a portion of the culture was taken, and trichloroacetic acid was added so as to give a final concentration of 5% to precipitate the cells. Each of the precipitates was collected by centrifugation and washed with acetone. Thereafter, the washed cells were dissolved in a sample buffer for SDS-PAGE, and proteins were separated by SDS-PAGE, followed by detection of induced chaperones by CBB staining (FIG. 2, left panel).

The cells of each of NK284 and NK287 recovered by centrifugation of the remaining portion of the culture mentioned above were disrupted by sonication. Thereafter, the disrupted cells were fractionated by centrifugation into a soluble fraction and an insoluble fraction to detect prourokinase in each fraction by Western blotting using an antibody against urokinase (manufactured by SANBIO BV) (FIG. 2, right panel).

Example 3

Preparation of pG-KJE6

The luciferase gene, located downstream of the Pzt-1 promoter in a plasmid pUHE2Pzt-1 (made available by Dr. H. Bujard of Heidelberg University, Germany), the plasmid pUHE2Pzt-1 carrying the Pzt-1 promoter, was cut out with restriction endonucleases KpnI and XbaI and ligated to the *E. coli* groE operon lacking its own promoter region, the *E. coli* groE operon being prepared by digesting pKV1561 [Kanemori, M. et al., *J. Bacteriol.* 176, 4235–4242 (1994)] with a restriction endonuclease XhoI, to prepare a plasmid pGro8 for expression of GroEL and GroES under the control of the Pzt-1 promoter. Subsequently, the tetracycline repressor (tetR) gene of about 800 bp was prepared from an *E. coli* strain having a transposon Tn10 by PCR, and the resulting gene was inserted into the AatI site upstream of the Pzt-1 promoter of pGro8, to give pGro10R.

Next, the resulting pGro10R was cleaved with restriction endonucleases SacI and AvrII to prepare a fragment containing tetR-Pzt-1-groESgroEL. The resulting fragment was then blunt-ended and inserted into the XmnI site of the pKJE7 prepared in Example 1, to prepare a plasmid pG-KJE6 for expression of DnaK, DnaJ and GrpE under the control of the arab promoter and for expression of GroEL and GroES under the control of Pzt-1.

Example 4

Induction Expression of Chaperone from pG-KJE6 in *E. coli* JM109

*E. coli* JM109 (TaKaRa Competent Cell, manufactured by Takara Shuzo Co., Ltd.) was transformed by the rubidium chloride method with 10 ng of the pG-KJE6 prepared in Example 3. The transformants resulting from selection with chloramphenicol were cultured at 30° C. in L broth supplemented with 0 to 3 mg/ml L-arabinose (manufactured by Wako Pure Chemical Industries) and 0 to 150 ng/ml tetracycline (manufactured by Nacalai Tesque). When Klett Unit reached about 40, trichloroacetic acid was added to the culture so as to give a final concentration of 5% to precipitate the cells. Each of the precipitates was collected by centrifugation and washed with acetone. Thereafter, the washed cells were dissolved in a sample buffer for SDS-PAGE, and proteins were separated by SDS-PAGE, followed by detection of induced chaperones by CBB staining (FIG. 3).

Example 5

Preparation of NK241 cotransformant

A region encoding mature CryjII protein ($Arg^{46}$-$Ser^{433}$) of a *Cryptomeria Japonica* pollen allergen CryjII cDNA [Namba, M. et al., FEBS Lett. 353, 124–128 (1994)] was inserted into the EcoRI-PstI site of the IPTG-inducible expression plasmid pKK223-3 for *E. coli* (manufactured by Pharmacia Biotech), to prepare pKCJ2. Subsequently, the $lacI^g$ gene prepared from pMJR1560 (manufactured by Amersham) was inserted into the BamHI site of pKCJ2 to give pKCJ2I.

*E. coli* MG1655 (CGSC6300; made available by *E. coli* Genetic Stock Center, Yale University) was transformed by the rubidium chloride method with 10 ng of the pG-KJE6 prepared in Example 3 and 10 ng of the CryjII expression vector pKCJ2I described above. The resulting cotransformants were isolated by selection with chloramphenicol and ampicillin and named as cotransformant NK241.

Example 6

Expression of CryjII Using NK241

NK241 prepared in Example 5 was cultured in the same manner as in Example 4, except that 0 to 8 mg/ml L-arabinose and 0 to 10 ng/ml tetracycline were added. When Klett Unit reached about 40, 1 mM IPTG was added to the culture. After culturing for two hours, a portion of the culture was taken, and trichloroacetic acid was added so as to give a final concentration of 5% to precipitate the cells. The precipitates were collected by centrifugation and washed with acetone. Thereafter, the washed cells were dissolved in a sample buffer for SDS-PAGE, and proteins were separated by SDS-PAGE, followed by detection of induced chaperones by CBB staining. Furthermore, CryjII was detected by Western blotting using a monoclonal antibody N-26 raised against CryjII [Sawatani et al., Allergy, 43, 467–473 (1984)] (FIG. 4).

Also, the NK241 cells recovered by centrifugation of the remaining portion of the culture were disrupted by sonication. Thereafter, the disrupted cells were fractionated by centrifugation into a soluble fraction and an insoluble fraction to detect CryjII in each fraction by Western blotting in the same manner as above (FIG. 5).

Example 7

Stability of CryjII Expressed in NK241

Figure 6:
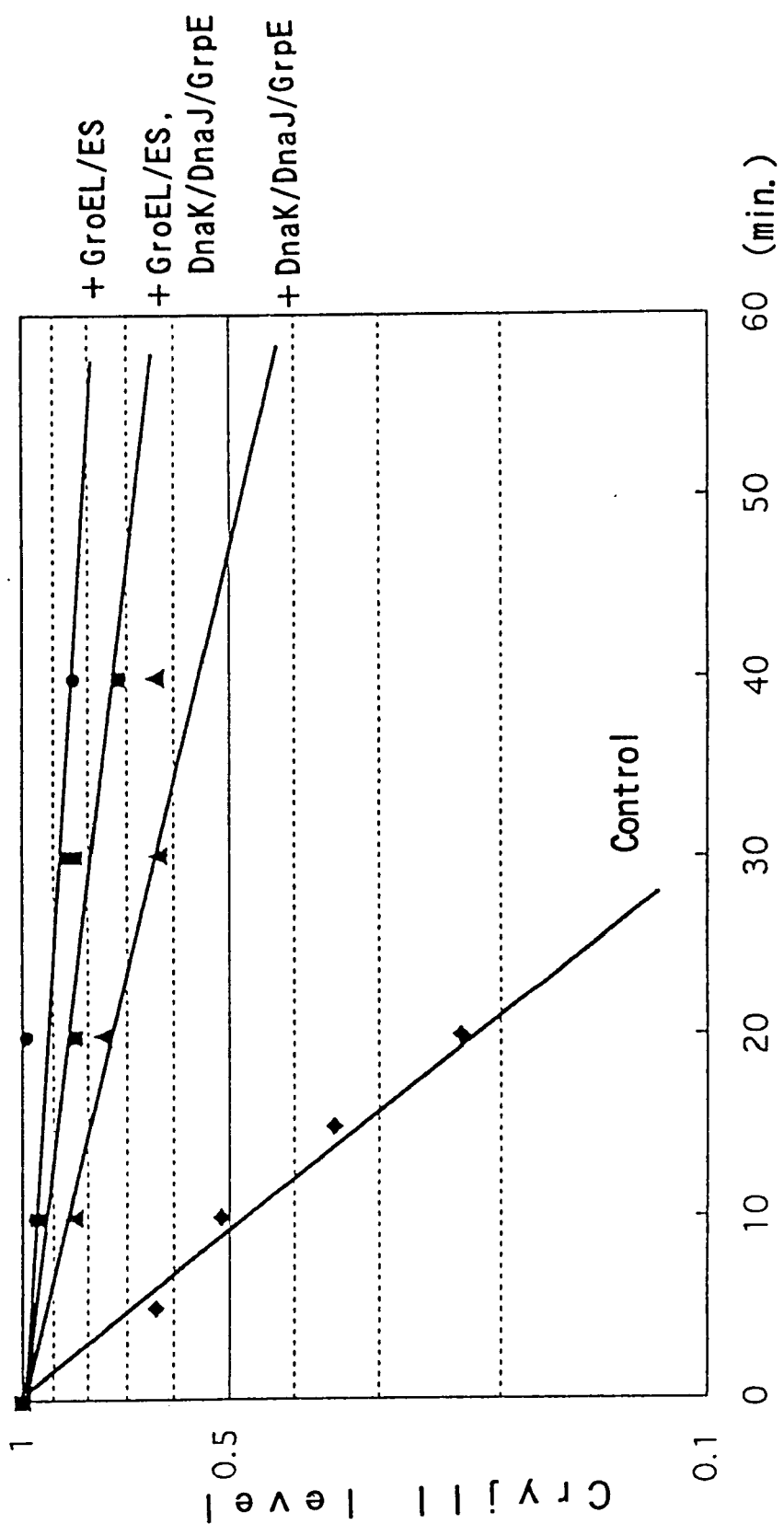
FIG. 6 is a graph showing the stability of CryjII coexpressed with various chaperones, wherein the CryjII level at 0 minute is defined as 1, and a half-life of CryjII level is defined as a time period in which the remaining CryjII level is 0.5 that of the initial level.

NK241 prepared in Example 5 was cultured in the same manner as in Example 4, except that 20 ng/ml tetracycline, or 8 mg/ml L-arabinose or both 20 ng/ml tetracycline and 8 mg/ml L-arabinose were added. When Klett Unit reached about 40, 1 mM IPTG was added to the culture. After culturing for two hours, expression of CryjII was induced. Spectinomycin (manufactured by Sigma) was then added so as to give a final concentration of 500 μg/ml to stop protein synthesis. Thereafter, samples were taken at given intervals, and cells were collected. A total protein of each of the cells was separated by SDS-PAGE, and Western blotting was then carried out using a monoclonal antibody N-26 raised against CryjII. The resulting Western blotting image was captured with a scanner, and the band intensity was assayed using an analytical software Intelligent Quantifier (manufactured by Nihon Bioimage) (FIG. 6).

Example 8

Expression of CryjII in Various Chaperone Mutants

E. coli MC4100 ΔdnaK52 [Nagai, H. et al., Proc. Natl. Acad. Sci. USA 91, 10280–10284 (1994)] was used as a DnaK mutant, E. coli MC4100 ΔdnaJ259 [Ishiai, M. et al., J. Bacteriol. 174, 5597–5603 (1992)] as a DnaJ mutant, E. coli MC4100 grpE280 [Ishiai, M. et al., J. Bacteriol. 174, 5597–5603 (1992)] as a GrpE mutant, E. coli MC4100 groEL44 [Tilly, K. and Georgopoulos, C., J. Bacteriol. 149, 1082–1088 (1982)] as a GroEL mutant, and E. coli MC4100 groES72 [Tilly, K. and Georgopoulos, C., J. Bacteriol. 149, 1082–1088 (1982)] as a GroES mutant. According to the method described in Example 5, 10 ng of the CryjII expression vector was introduced into each of these mutants, and the expression and solubility of CryjII in each mutant were examined in the same manner as in Example 6 (FIG. 7).

Example 9

Expression of CryjII in rpoH Deletion Mutant

The ΔrpoH::kan gene of E. coli MC4100 ΔrpoH [Zhou, Y. N. et al., J. Bacteriol. 170, 3640–3649 (1988)] was transferred into E. coli MG1655 by transduction using T4 phage. A strain having ΔrpoH::kan transferred thereinto was selected using kanamycin resistance as an index. Having confirmed that the strain grew at 20° C., while it could not grow at 30° C., 37° C. or 42° C., E. coli MG1655 ΔrpoH strain, NK161, was obtained.

Same procedures as in Example 5 were carried out, except that E. coli MG1655 ΔrpoH strain, NK161, described above was used in place of E. coli MG1655 in Example 5, to give an rpoH deletion mutant cotransformant NK196. The expression and solubility of CryjII were examined for the resulting deletion mutant cotransformant in the same manner as in Example 6 (FIGS. 8 and 9).

Example 10

Preparation of NK269 Cotransformant

A region encoding mature ORP150 protein ($Leu^{33}$–$Leu^{999}$) of a human ORP150 cDNA [Ikeda, J. et al., Biochem. Biophys. Res. Comm. 230, 94–99 (1997)] was inserted into the NcoI site of the IPTG-inducible expression plasmid pTrc99A for E. coli (manufactured by Pharmacia Biotech) to prepare pORP4. E. coli JM109 was transformed with 10 ng of resulting pORP4 and 10 ng of pG-KJE6 prepared in Example 3 according to the method described in Example 4, to give a cotransformant NK269.

Example 11

Expression of Human ORP150 Using NK269

Since NK269 prepared in Example 10 could not grow when L-arabinose was added to the culture at the initiation time of cultivation, NK269 was cultured to induce expression of human ORP150 in the same manner as Example 6, except that L-arabinose and tetracycline were added when Klett Unit reaches about 40 (FIG. 10).

According to the present invention, there can be provided an operon comprising polynucleotides encoding chaperones which can be used for expressing a foreign protein in E. coli cells in a stabilized and solubilized form, a plasmid for expression having the operon, a cotransformant prepared by introducing the plasmid into E. coli together with an expression vector for a foreign protein, and a method for producing a foreign protein using the cotransformant. According to the present invention, an efficient production of a foreign protein in E. coli by means of genetic engineering techniques is made possible.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An artificial operon comprising polynucleotides encoding each of chaperones DnaK, DnaJ and GrpE, wherein said artificial operon is a single operon having a single promoter.

2. The artificial operon according to claim 1, wherein said single promoter is inducible.

3. The artificial operon according to claim 2, wherein said inducible promoter is selected from the group consisting of lac, trp, araB and Pzt-1.

4. A plasmid comprising the artificial operon according to any one of claims 1 to 3, wherein said plasmid expresses DnaK, DnaJ and GrpE.

5. The plasmid according to claim 4, further comprising a groE operon having a single promoter, wherein the plasmid expresses DnaK, DnaJ, GrpE, GroEL and GroES.

6. A plasmid according to claim 5, wherein said promoter of said groE operon is inducible.

7. The plasmid according to claim 6, wherein said inducible promotor of said groE operon is selected from the group consisting of lac, trp, araB and Pzt-1.

8. A cotransformant obtainable by introducing the plasmid according to claim 5 into an *E coli* host cell together with an expression vector for foreign protein.

9. A cotransformant obtainable by introducing the plasmid according to claim 4 into an *E. coli* host cell together with an expression vector for a foreign protein.

10. The cotransformant according to claim 7, wherein said *E. coli* host cell is a protease mutant.

11. The cotransformant according to claim 10, wherein the protease mutant is a lon-clpPX double mutant or a lon-clpPX-hslV/U triple mutant.

12. The cotransformant according to claim 9, wherein said *E. coli* host cell is a plsX mutant.

13. The cotransformant according to claim 9, wherein said *E. coli* host cell is an rpoH mutant.

14. The cotransformant according to claim 13, wherein said rpoH mutant is an rpoH deletion mutant.

15. The cotransformant according to claim 9, wherein said foreign protein is selected from the group consisting of interferons, interleukins, interleukin receptors, interleukin receptor antagonists, granulocyte colony-stimulating factors, granulocyte macrophage colony-stimulating factors, macrophage colony-stimulating factors, erythropoietin, thrombopoietin, leukemia inhibitors, stem cell growth factors, tumor necrosis factors, growth hormones, proinsulin, insulin-like growth factors, fibroblast growth factors, platelet-derived growth factors, transforming growth factors, hepatocyte growth factors, bone morphogenetic factors, nerve growth factors, ciliary neurotrophic factors, brain-derived neurotrophic factors, glia cell line-derived neurotrophic factors, neurotrophine, prourokinase, tissue plasminogen activators, blood coagulation factors, protein C, glucocerebrosidase, superoxide dismutase, renin, lysozyme, P450, prochymosin, trypsin inhibitors, elastase inhibitors, lipocortin, reptin, immunoglobulins, single-chain antibodies, complement components, serum albumin, cedar pollen allergens, hypoxia-induced stress proteins, protein kinases, proto-oncogene products, transcription factors and virus-constituent proteins.

16. A method for producing a foreign protein comprising the steps of:

culturing the cotransformant according to claim 9 under conditions which allow expression of said foreign protein; and collecting said foreign protein from culture.

17. The method according to claim 16, wherein the cotransformant is cultured under the conditions wherein the expression levels of DnaK, DnaJ and GrpE, and the expression levels of GroEL and GroES are at levels suitable for stabilization and/or solubilization of the foreign protein.

18. A cotransformant obtainable by introducing a plasmid comprising an artificial operon comprising polynucleotides encoding each of chaperones DnaK, DnaJ and GrpE into a protease mutant *E. coli* host cell together with an expression vector for a foreign protein.

19. The cotransformant according to claim 18, wherein the protease mutant is a lon-clpPX double mutant or a lon-clpPX-hslV/U triple mutant.

20. A cotransformant obtainable by introducing a plasmid comprising an artificial operon comprising polynucleotides encoding each of chaperones DnaK, DnaJ and GrpE into a plsX mutant *E. coli* host cell together with an expression vector for a foreign protein.

21. A cotransformant obtainable by introducing a plasmid comprising an artificial operon comprising polynucleotides encoding each of chaperones DnaK, DnaJ and GrpE into a rpoH mutant *E. coli* host cell together with an expression vector for a foreign protein.

22. The cotransformant according to claim 21, wherein said rpoH mutant is an rpoH deletion mutant.

23. A method for producing a foreign protein comprising culturing a cotransformant obtainable by introducing a plasmid comprising an artificial operon comprising polynucleotides encoding each of chaperones DnaK, DnaJ and GrpE, further comprising a groE operon ligated to an inducible promoter, into an *E. coli* host cell together with an expression vector for a foreign protein, wherein the cotransformant is cultured under the conditions wherein expression levels of DnaK, DnaJ and GrpE, and the expression levels of GroEL and GroES are at levels suitable for stabilization and/or solubilization of the foreign protein.

* * * * *